United States Patent [19]

Brown et al.

[11] 4,285,954

[45] Aug. 25, 1981

[54] PESTICIDAL S-PYRIDYL THIOESTERS OF PHENYLBUTANOIC ACIDS AND DERIVATIVES THEREOF

[75] Inventors: Thomas L. Brown, Mountain View; Clive A. Henrick, Palo Alto, both of Calif.

[73] Assignee: Zoecon Corporation, Palo Alto, Calif.

[21] Appl. No.: 208,469

[22] Filed: Nov. 19, 1980

[51] Int. Cl.$^3$ ................. C07D 213/83; C07D 405/12; A61K 31/44
[52] U.S. Cl. ................................. 424/263; 546/270; 546/301; 546/302

[58] Field of Search ...................... 546/301, 270, 302; 424/263

[56] References Cited

U.S. PATENT DOCUMENTS

| | | | |
|---|---|---|---|
| 4,172,135 | 10/1979 | Kristiansen et al. | 546/301 |
| 4,223,033 | 9/1980 | Henrick | 546/300 |
| 4,226,872 | 10/1980 | Henrick | 424/263 |

*Primary Examiner*—Alan L. Rotman
*Attorney, Agent, or Firm*—Donald W. Erickson

[57] ABSTRACT

S-pyridyl thioesters of aliphatic acids, synthesis thereof and the use of said S-thioesters for the control of pests.

6 Claims, No Drawings

PESTICIDAL S-PYRIDYL THIOESTERS OF PHENYLBUTANOIC ACIDS AND DERIVATIVES THEREOF

This invention relates to novel S-thioesters of aliphatic acids, synthesis thereof, and the use of said thioesters for the control of pests.

The S-thioesters of the present invention are represented by the following formula (A):

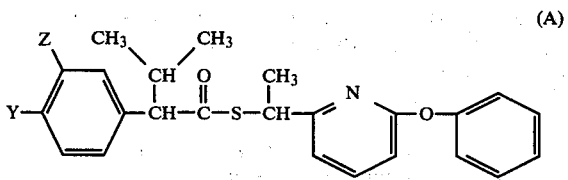

wherein,

Y is hydrogen, lower alkyl of one to four carbon atoms, lower alkoxy of one to four carbon atoms, bromo, chloro, difluoromethoxy, trifluoromethoxy or trifluoromethyl; and Z is independently selected from the values of Y; or Y and Z together form a methylenedioxy or a difluoromethylenedioxy group.

In the description hereinafter and the appended claims, Y and Z are as defined hereinabove, unless otherwise specified.

The compounds of the present invention of formula (A) are useful agents for the control of pests such as insects or acarids. The S-thioesters of formula (A) herein have been found to possess greatly improved pesticidal activity as compared to the corresponding carboxylic acid esters.

The compounds of formula (A) can be synthesized as outlined below.

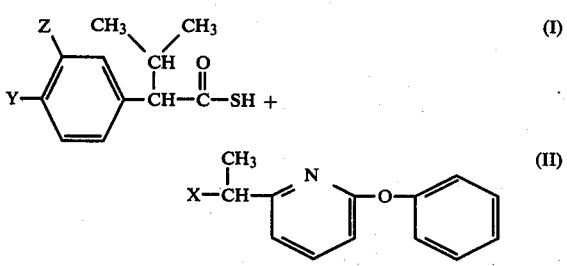

In the general practice of the above synthesis, a thioacid of formula (I) is reacted with a halide of formula (II) (wherein X=Br or Cl) to form the S-thioester (A). The reaction is conducted in an organic solvent such as hexamethylphosphoric triamide dimethylformamide, N-methylpyrrolidone or the like in the presence of potassium carbonate, usually at an elevated temperature above room temperature.

The thioacid (I) is prepared by reacting the corresponding carboxylic acid (III) with sodium hydrosulfide in an organic solvent such as dimethylformamide in the presence of triethylamine and ethyl chloroformate at a temperature below room temperature. The carboxylic acids of formula (III) are described by Fujimoto et al., U.S. Pat. No. 3,996,244.

The alcohols corresponding to formula (LL) (where X=OH) are described by Henrick, U.S. Pat. No. 4,226,872. The alcohols are then halogenated by conventional procedures to give the compounds of formula (II) where X=Br or Cl.

In another embodiment, the compounds of formula (A) can be prepared by reacting an acid of formula (III) with a thiol of formula (IV).

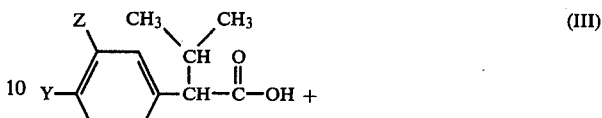

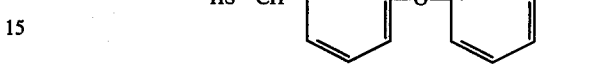

The above reaction is carried out in the presence of, for example, 4-dimethylaminopyridine and dicyclohexylcarbodiimide. The thiol (IV) can be prepared by first reacting a halide of formula (II) (wherein X=Br or Cl) with sodium hydrosulfide and hydrogen sulfide in the presence of a solvent such as ethanol. The intermediate product (V) is reacted with a reducing agent such as zinc in acetic acid to give the thiol of formula (IV).

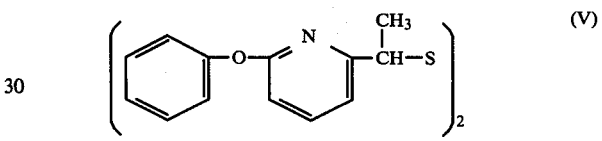

The compounds of the present invention of formula (A) have one or more asymmetric carbon atoms. The present invention includes each of the optical isomers and racemic mixtures thereof. In the examples hereinafter, unless otherwise specified, the compound prepared is a racemic mixture.

The compounds of the present invention of formula (A) are useful pest control agents, particularly for the control of insects and acarids. In the use of the compounds of formula (A) for combating insects and acarids for the protection of agricultural crops, for example soybeans, cotton, alfalfa, etc. a compound of formula (A), or mixtures thereof, together with a carrier is applied to the locus in a pesticidally effective amount. The carrier can be liquid or solid and include adjuvants such as wetting agents, dispersing agents and other surface active agents. The compounds of formula (A) can be used in formulations such as wettable powders, solutions, dusts, granules, emulsifiable concentrates, and the like. Suitable solid carriers include natural and synthetic silicates and clays, carbon or charcoal granules, natural and synthetic resins, waxes, and the like. Suitable liquid carriers include water, aromatic hydrocarbons, alcohols, vegetable and mineral oils, ketones, and the like. The amount of a compound of formula (A) in the formulation can vary widely, generally within the range of about 0.01 percent to about 90.0 percent, by weight.

The compounds of the present invention are effective on many different insects and on acarids. The compounds are effective control agents for insects such as mosquitoes, flies, aphids, weevils and acarids such as the spider mite and ticks. Depending upon the particular combination of the substituents of formula (A) herein, the compounds have a broad or relatively narrow spectrum of unusually high pesticidal activity on insects and acarids. Among the pests against which the compounds of the present invention are pesticidally effective are insects of the order Lepidoptera, Orthoptera, Heteroptera, Homoptera, Diptera, Coleoptera or Hymenoptera, and acarids of the order Acarina including mites of the family Tetranychidae or Tarsonemidae and ticks such as Ornithodoros.

The compounds of the present invention can be used in combination with other pesticides such as the carbamates, phosphates and insect growth regulators, e.g. propoxur, carbaryl, naled, dichlorvos, methoprene, kinoprene, hydroprene, cyhexatin and resmethrin.

The following examples are provided to illustrate the practice of the present invention. Temperature is given in degrees Centigrade. RT means room temperature.

EXAMPLE 1

Three grams (14.1 mmol) of 2-(4-chlorophenyl)-3-methylbutanoic acid is dissolved in approximately 50 ml of dry dimethylformamide, after which 1.43 g (14.1 mmol) of triethylamine is added in one portion. The solution is cooled to 0° and 1.59 g (14.1 mmol) of ethyl chloroformate is slowly added over 30 seconds. After 0.5 hour 3.15 g (28.2 mmol) of sodium hydrosulfide is added. The mixture is stirred overnight at room temperature. The reaction mixture is then poured into 150 ml of water and adjusted to pH 3 with 5% aqueous sulfuric acid. Extraction with 50 ml methylene chloride (3×) is followed by drying and stripping. Dimethylforamide is still present, so the product is taken up in ether and washed with 200 ml of water, dried and stripped to yield 2-(4-chlorophenyl)-3-methylbutanethioic S-acid.

2-(4-Chlorophenyl)-3-methylbutanethioic S-acid (0.41 g., 1.8 mmol), α-methyl(6-phenoxy-2-pyridyl)-methyl bromide (0.5 g, 1.8 mmol) and potassium carbonate (0.5 g, 3.6 mmol) are dissolved in 10 ml of hexamethylphosphoric triamide, and the mixture is heated, under nitrogen, to 50°–60° overnight. The reaction mixture is then poured into 100 ml of water and extracted with ether (3×). The combined organic phases are washed with water (2×) and with brine, dried and stripped. The crude product is purified by preprarative thin layer chromatography (silica gel, developing with 10% ethyl acetate/hexane) to yield S-α-methyl(6-phenoxy-2-pyridyl)methyl 2-(4-chlorophenyl)-3-methylbutanethioate, MS m/e 425 (M+) 125.1 (100).

EXAMPLE 2

Into 2.7 g (7.9 mmol) of α-methyl(6-phenoxy-2-pyridyl) methyl bromide dissolved in 40 ml of absolute ethanol is slurried 2.1 g (9.5 mmol) of sodium hydrosulfide. The mixture is saturated with hydrogen sulfide, heated to 50° for 36 hours and then stirred at RT for 48 hours. The reaction mixture is poured into 200 ml of water and acidified with 10% aqueous hydrochloric acid. It is extracted with methylene chloride (3×), dried and stripped to give 1,1'-bis-(6-phenoxy-pyridine-2-yl)diethyldisulfide.

1.2 Grams (2.64 mmol) of 1,1'-bis-(6-phenoxy-pyridine-2-yl)diethyldisulfide and 0.67 g (10.4 mmol) of zinc are slurried in 20 ml of glacial acetic acid and the system is purged with nitrogen for 30 minutes. The slurry is then heated to reflux. After approximately 4 hours at reflux temperature, the mixture is allowed to cool to RT and is stirred overnight. The mixture is then poured into 200 ml of water and extracted with methylene chloride (3×). The combined extracts are washed with water (2×), dried over magnesium sulfate, filtered through celite and stripped to give α-methyl(6-phenoxy-2-pyridyl)methanethiol.

2-(4-Difluoromethoxyphenyl)-3-methylbutanoic acid (1.8 mmol), α-methyl(6-phenoxy-2-pyridyl)methanethiol (1.5 mmol) and 20 mg of 4-dimethylaminopyridine are dissolved in 15 ml of dry methylene chloride. Dicyclohexylcarbodiimide (1.6 mmol) is added in one portion and the mixture is stirred overnight. The mixture is then diluted with 30 ml of ether, filtered and stripped. The crude product is purified by preparative thin layer chromatography (silica gel, developing with 10% ethyl acetate/hexane) to yield S-α-methyl(6-phenoxy-2-pyridyl)methyl 2-(4-difluoromethoxyphenyl)-3-methylbutanethioate.

EXAMPLE 3

Following the procedure of Example 1, each of the thioacids of column I is reacted with α-methyl(6-phenoxy-2-pyridyl)-methyl bromide or chloride, giving the corresponding thioesters of column II.

I 2-(4-methoxyphenyl)-3-methylbutanethioic S-acid
2-(3-chlorophenyl)-3-methylbutanethioic S-acid
2-(4-bromophenyl)-3-methylbutanethioic S-acid
2-(3,4-dimethylphenyl)-3-methylbutanethioic S-acid
2-(4-t-butylphenyl)-3-methylbutanethioic S-acid
2-(4-trifluoromethoxyphenyl)-3-methylbutanethioic S-acid
2-(3,4-methylenedioxyphenyl)-3-methylbutanethiolic S-acid
2-(3-methoxyphenyl)-3-methylbutanethioic S-acid
2-(4-trifluoromethylphenyl)-3-methylbutanethioic S-acid
2-(3,4-difluoromethylenedioxyphenyl)-3-methylbutanethioic S-acid

II

S-α-methyl(6-phenoxy-2-pyridyl)methyl 2-(4-methoxyphenyl)-3-methylbutanethioate
S-α-methyl(6-phenoxy-2-pyridyl)methyl 2-(3-chlorophenyl)-3-methylbutanethioate
S-α-methyl(6-phenoxy-2-pyridyl)methyl 2-(4-bromophenyl)-3-methylbutanethioate
S-α-methyl(6-phenoxy-2-pyridyl)methyl 2-(3,4-dimethylphenyl)-3-methylbutanethioate
S-α-methyl(6-phenoxy-2-pyridyl)methyl 2-(4-t-butylphenyl)-3-methylbutanethioate
S-α-methyl(6-phenoxy-2-pyridyl)methyl 2-(4-trifluoromethoxyphenyl)-3-methylbutanethioate
S-α-methyl(6-phenoxy-2-pyridyl)methyl 2-(3,4-methylenedioxyphenyl)-3-methylbutanethioate
S-α-methyl(6-phenoxy-2-pyridyl)methyl 2-(3-methoxyphenyl)-3-methylbutanethioate
S-α-methyl(6-phenoxy-2-pyridyl)methyl 2-(4-trifluoromethylphenyl)-3-methylbutanethioate
S-α-methyl(6-phenoxy-2-pyridyl)methyl 2-(3,4-difluoromethylenedioxyphenyl)-3-methylbutanethioate The S-thioesters of column II may alternately be prepared by following the methods of Example 2 by reacting each of the carboxylic acids of column III with α-methyl(6-phenoxy-2-pyridyl)methanethiol.

III 2-(4-methoxyphenyl)-3-methylbutanoic acid
2-(3-chlorophenyl)-3-methylbutanoic acid
2-(4-bromophenyl)-3-methylbutanoic acid 2-(3,4-dimethylphenyl)-3-methylbutanoic acid
2-(4-t-butylphenyl)-3-methylbutanoic acid
2-(4-trifluoromethoxyphenyl)-3-methylbutanoic acid
2-(3,4-methylenedioxyphenyl)-3-methylbutanoic acid
2-(3-methoxyphenyl)-3-methylbutanoic acid
2-(4-trifluoromethylphenyl)-3-methylbutanoic acid
2-(3,4-difluoromethylenedioxyphenyl)-3-methylbutanoic acid

EXAMPLE 4

A. Two groups of 10 each of 0–24 hr III instar *Heliothis virescens* larvae were treated with 1 μl of the test compound [S-α-methyl(6-phenoxy-2-pyridyl)methyl 2-(4-chlorophenyl)-3-methylbutanethioate] in acetone at different dosage rates by application to the dorsum of the thorax. Two groups of 10 each were treated identically with 1 μl acetone as controls. Larvae are held individually in 30 ml plastic cups provided with artificial medium for 72 hours at 25° and 16 hr photoperiod. After 72 hr the number of dead is calculated as a percentage of the total number originally treated and then corrected for any mortality in the control group using Abbott's formula. The toxicity is expressed as $LD_{50}$, which is the dosage, in μg per insect, required to kill 50% of the test insects.

The activity of the above compound of the present invention (1) is compared with that of the prior art compound (6-phenoxy-2-pyridyl)methyl 2-(4-chlorophenyl)-3-methylbutanoate (2), disclosed by Malhotra and Van Heertum, U.S. Pat. No. 4,228,172, following the above procedure. Results are shown in Table I.

B. Fifteen 72-hr-old adult female *Musca domestica* L. are anesthetized with ether vapor. These are then treated with 1 μl of the test compound diluted to different dosage rates in acetone applied to the dorsal surface of the prothorax. They are held in an assay container with milk-saturated cotton at 25°, 16 hr photoperiod for 24 hours. The effect is stated as the number dead calculated as a percentage of the total, corrected for any control mortality using Abbott's formula. The toxicity is expressed as $LD_{50}$.

Results of the testing of the compound S-α-methyl(6-phenoxy-2-pyridyl)methyl 2-(4-chlorophenyl)-3-methylbutanethioate (1) and (6-phenoxy-2-pyridyl)methyl 2-(4-chlorophenyl)-3-methylbutanoate (2) are presented in Table I.

TABLE I

| COMPOUND | BIOASSAY RESULTS (in μg/insect) | |
| --- | --- | --- |
| | *H. virescens* | *M. domestica* |
| 1 | 0.026 | 0.120 |
| 2 | 0.200 | 0.320 |

What is claimed is:

1. A compound of the following formula (A):

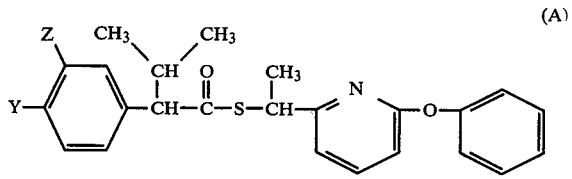

wherein,

Y is hydrogen, lower alkyl of one to four carbon atoms, lower alkoxy of one to four carbon atoms, bromo, chloro, difluoromethoxy, trifluoromethoxy or trifluoromethyl; and Z is independently selected from the values of Y; or Y and Z together form a methylenedioxy or a difluoromethylenedioxy group.

2. A compound according to claim 1 wherein Z is hydrogen and Y is methyl, methoxy, t-butyl, chloro, difluoromethoxy, trifluoromethoxy or trifluoromethyl.

3. The compound S-α-methyl(6-phenoxy-2-pyridyl)methyl 2-(4-chlorophenyl)-3-methylbutanethioate, according to claim 2.

4. A compound according to claim 1 wherein Y is hydrogen and Z is methyl, methoxy or chloro.

5. A method for controlling insects or acarids which comprises applying to the locus a pesticidally effective amount of a compound of claim 1.

6. A method according to claim 5 wherein the compound is S-α-methyl(6-phenoxy-2-pyridyl)methyl 2-(4-chlorophenyl)-3-methylbutanethioate.

* * * * *